US00PP25426P2

(12) United States Plant Patent
Hartman

(10) Patent No.: US PP25,426 P2
(45) Date of Patent: Apr. 7, 2015

(54) ***CALADIUM* PLANT NAMED 'FLARE'**

(50) Latin Name: *Caladium×hortulanum*
Varietal Denomination: Flare

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 130 days.

(21) Appl. No.: 13/986,556

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Flare', characterized by its compact, upright and uniformly mounding plant habit; vigorous growth habit and rapid growth rate; lance-type leaves that are shiny in luster with rose red-colored centers surrounded by a greyed green and pink-colored speckling and dark green-colored margins; and good landscape performance.

4 Drawing Sheets

Botanical designation: *Caladium×hortulanum.*
Cultivar denomination: 'FLARE'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'Flare'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2007 in Lake Placid, Fla. of *Caladium×hortulanum* 'White Christmas', not patented, as the female, or seed, parent with *Caladium×hortulanum* 'Rosemary', disclosed in U.S. Plant Pat. No. 20,993, the male, or pollen, parent. The new *Caladium* plant was discovered and selected by the Inventor as a single plant within the progeny of the stated cross-pollination in a controlled outdoor nursery environment in Zolfo Springs, Fla. on Sep. 15, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since Apr. 15, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Flare'. These characteristics in combination distinguish 'Flare' as a new and distinct *Caladium* plant:

1. Compact, upright and uniformly mounding plant habit.
2. Vigorous growth habit and rapid growth rate.
3. Lance-type leaves that are shiny in luster with rose red-colored centers surrounded by a greyed green and pink-colored speckling and dark green-colored margins.
4. Good landscape performance.

Plants of the new *Caladium* differ primarily from plants of the female parent, 'White Christmas', in leaf shape and color as plants of 'White Christmas' have broad fancy-type white-colored leaves with distinct dark green-colored venation and margins. In addition, plants of the new *Caladium* are more compact than plants of 'White Christmas'.

Plants of the new *Caladium* differ primarily from plants of the male parent, 'Rosemary', in leaf and leaf petiole color as plants of 'Rosemary' have leaves that are darker rose red in color with mottled light and dark green-colored borders and leaf petioles that are tan pink to tan green in color with greenish brown-colored stippling. In addition, plants of the new *Caladium* are more compact than plants of 'Rosemary'.

Plants of the new *Caladium* can be compared to plants of *Caladium×hortulanum* 'Florida Sweetheart', disclosed in U.S. Plant Pat. No. 8,526. In side-by-side comparisons, plants of the new *Caladium* differed primarily from plants of 'Florida Sweetheart' in the following characteristics:

1. Plants of the new *Caladium* were more upright than plants of 'Florida Sweetheart'.
2. Plants of the new *Caladium* grew faster and produced finished plants about one week earlier than plants of 'Florida Sweetheart'.
3. Plants of the new *Caladium* and 'Florida Sweetheart' differed in leaf luster and coloration as leaves of plants of 'Florida Sweetheart' were dull and had lighter rose red-colored centers and dark green-colored margins.

Plants of the new *Caladium* can be compared to plants of *Caladium×hortulanum* 'Pink Symphony', not patented. In side-by-side comparisons, plants of the new *Caladium* differed primarily from plants of 'Pink Symphony' in the following characteristics:

1. Plants of the new *Caladium* were more compact than plants of 'Pink Symphony'.
2. Plants of the new *Caladium* grew faster and produced finished plants about one to two weeks earlier than plants of 'Pink Symphony'.
3. Plants of the new *Caladium* had broader leaves than plants of 'Pink Symphony'.
4. Plants of the new *Caladium* and 'Pink Symphony' differed in leaf luster and coloration as leaves of plants of 'Pink Symphony' were dull with mostly pink or pale pink-colored centers surrounded by a green-colored border with white to greenish white-colored venation.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Flare' in a 15-cm container and grown in a shadehouse.

The photograph at the top of the second sheet is a comparison view of typical plants of 'Flare' grown in 15-cm containers; the plant on the left has not had its tuber de-eyed and the plant on the right has had its tuber de-eyed prior to planting.

The photograph at the bottom of the second sheet is a close-up view of a typical inflorescence of 'Flare'.

The photograph at the top of the third sheet is a close-up view of typical freshly-harvested tubers and roots of 'Flare'.

The photograph at the bottom of the third sheet is a close-up view of typical plants of 'Flare' grown in an open field.

The photograph at the top of the fourth sheet is a comparison view of typical potted plants of 'Florida Sweetheart' (left), 'Flare' (center) and 'Pink Symphony' (right).

The photograph at the bottom of the fourth sheet is a comparison view of typical potted plants of the female parent, 'White Christmas' (left), 'Flare' (center) and the male parent, 'Rosemary' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Flare'.

Parentage:

*Female, or seed, parent.*—*Caladium×hortulanum* 'White Christmas', not patented.

*Male, or pollen, parent.*—*Caladium×hortulanum* 'Rosemary', disclosed in U.S. Plant Pat. No. 20,993.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments ovate to elliptic in shape. Height: About 2.6 cm. Diameter: About 3.6 cm. Segment height: About 2 cm. Segment diameter: About 1.4 cm. Texture: Thick, starchy; somewhat brittle. Color: Epidermis, freshly-harvested: Close to 199A and N199B. Epidermis, dried: Close to 200A to 200B. Cortical tissue: Close to 2C to 2D. Axillary buds: Close to 27C. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Compact, upright and uniformly mounding plant habit; vigorous and dense growth habit; rapid growth rate, potted plants in finished or saleable form in about six to seven weeks after planting tubers; leaf petioles and leaves arise from one or more growing points on tubers; petioles mostly upright and arching outwardly with development.

*Plant height, from soil level to top of foliar plane, shadehouse-grown potted plants.*—About 26 cm to 30 cm.

*Plant height, from soil level to top of inflorescences, shadehouse-grown potted plants.*—About 37 cm.

*Plant diameter or spread, shadehouse-grown potted plants.*—About 39 cm to 44 cm.

*Number of clumps per plant, shadehouse-grown potted plants.*—About three to four from de-eyed tubers.

*Cataphylls, shadehouse-grown potted plants.*—Length: About 4 cm to 6.5 cm. Width: About 1 cm to 1.8 cm. Shape: Wedge-shaped. Apex: Acuminate. Base: Sheathing the stem. Color, outer surface: Close to N170D and N170D tinged with close to 182D; stippled, streaked and tessellated with close to 200C and faintly tinged with close to 147D; with development, color becoming closer to 200D. Color, inner surface: Close to N155C; outer surface colors and patterns visible.

Foliage description:

*Arrangement and type.*—Alternate; simple; lance-type.

*Length, shadehouse-grown potted plants.*—About 16 cm to 20 cm.

*Width, shadehouse-grown potted plants, flattened.*—About 10.9 cm to 13 cm.

*Shape.*—Ovate.

*Apex.*—Acute.

*Base*.—Sagittate, peltate; cordate.

*Margin*.—Entire; wavy with broad undulations.

*Texture, upper surface*.—Smooth, glabrous; leathery; shiny in luster.

*Texture, lower surface*.—Smooth, glabrous; glaucous.

*Venation pattern*.—Pinnate.

*Color, shadehouse-grown potted plants*.—Developing leaves, upper and lower surfaces: Background color: Central areas, close to 185B tinged with close to 53B and 182A to 182B; marginal areas, close to 183A; margins, close to 147A. Basal notch: Close to 187A. Venation: Close to 53B and 187B. Fully expanded leaves, upper surface: Background color: Central areas, close to 185B tinged with close to 53B with flecking close to 182A to 182B; marginal areas, close to 183A with flecking close to 157A, 147C, 184B and 182A to 182B; margins, close to 147A and 139A. Basal notch: Close to 187A. Venation: Close to 53B and 187C. Fully expanded leaves, lower surface: Background color: Central areas, close to 184B to 184C with flecking close to 160D and 182D; marginal areas, close to 184A to 184B with flecking close to 160D; margins, close to 187B. Basal notch: Close to 187B. Venation: Close to 184A tinged with close to 53B.

*Petiole*.—Aspect: Initially upright and straight; with development, leaning outwardly and curving; flexible. Length, shadehouse-grown potted plants: About 16 cm to 27 cm. Diameter, distal, shadehouse-grown potted plants: About 4 mm. Diameter, proximal, shadehouse-grown potted plants: About 5 mm to 8 mm. Color, shadehouse-grown potted plants: Close to N170D and N170D tinged with close to 182D, stippled, streaked and tessellated with close to 200C and faintly tinged with close to 147D; distally, close to 51 C stippled, streaked and tessellated with close to 184C to 184D. Wing length, shadehouse-grown potted plants: About 3.5 cm to 10.2 cm. Wing diameter, shadehouse-grown potted plants: About 4 mm to 9 mm. Wing color, shadehouse-grown potted plants, outer surface: Close to N170D and N170D tinged with close to 182D, stippled, streaked and tessellated with close to 200C and faintly tinged with close to 147D. Wing color, shadehouse-grown potted plants, inner surface: Close to N155C; outer surface colors and patterns visible.

Inflorescence description: Inflorescences observed on ten week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Strongly night fragrant; sweet jasmine-like fragrance with camphor-like notes.

*Natural flowering season and flower longevity*.—Plants of the new *Caladium* typically flower during the spring or early summer in central Florida; flowers develop about ten weeks after growth commences; inflorescences last about three days before fading; inflorescences persistent.

*Spathe*.—Length, overall: About 12.5 cm. Length, distal open portion: About 8.7 cm. Length, proximal closed portion: About 3.8 cm. Width, distal open portion: About 2.2 cm. Width, at constriction: About 1 cm. Width, proximal closed portion: About 2 cm. Shape: Ovate. Apex: Acute. Base: Tapering to the peduncle. Margin: Entire. Texture, front and rear surfaces: Smooth, glabrous. Color, front surface: Distal open portion: Close to 160D and 159D; proximally speckled with close to 60B; with development, color becoming closer to N199B. Proximal closed portion: Close to 138C and 147C; towards the base, heavily tinged with close to 187A and 187C to 187D; color does not change with development. Color, rear surface: Distal open portion: Close to 160D and 157C to 157D. Proximal closed portion: Close to 195B to 195C, 160D and 147D with areas tinged with close to 181D and 183D.

*Spadix*.—Length: About 7.7 cm. Length, male flower zone: About 5.8 cm. Length, sterile zone: Less than 1 cm. Length, female flower zone: About 1.9 cm. Diameter, male flower zone: About 9 mm. Diameter, sterile flower zone: About 7 mm. Diameter, female flower zone: About 1 cm. Shape: Columnar, spindle-shaped. Apex: Obtuse. Base: Obtuse. Aspect: Upright. Color, mature, male zone: Close to 159D. Color, mature, sterile zone: Close to 159D. Color, mature, female zone: Close to 19C to 19D. Male flowers: Quantity per spadix: About 105. Shape: Obovate. Height: About 3 mm. Diameter: About 3.5 mm. Pollen amount: Abundant. Pollen color: Close to 5D. Female flowers: Quantity per spadix: About 115. Shape: Obovate. Height: About 3 mm. Diameter: About 1.5 mm. Stigma color: Close to 158B. Ovary color: Close to 155C.

*Scape*.—Length: About 24.5 cm. Diameter: About 6 mm. Strength: Sturdy; flexible. Aspect: Mostly erect. Texture: Smooth, glabrous; glaucous. Color: Close to 199D tinged with close to N170D and stippled, streaked and tessellated with close to 177A to 177B; distally, close to 147B to 147C tinged with close to 183C to 183D.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Flare' as illustrated and described.

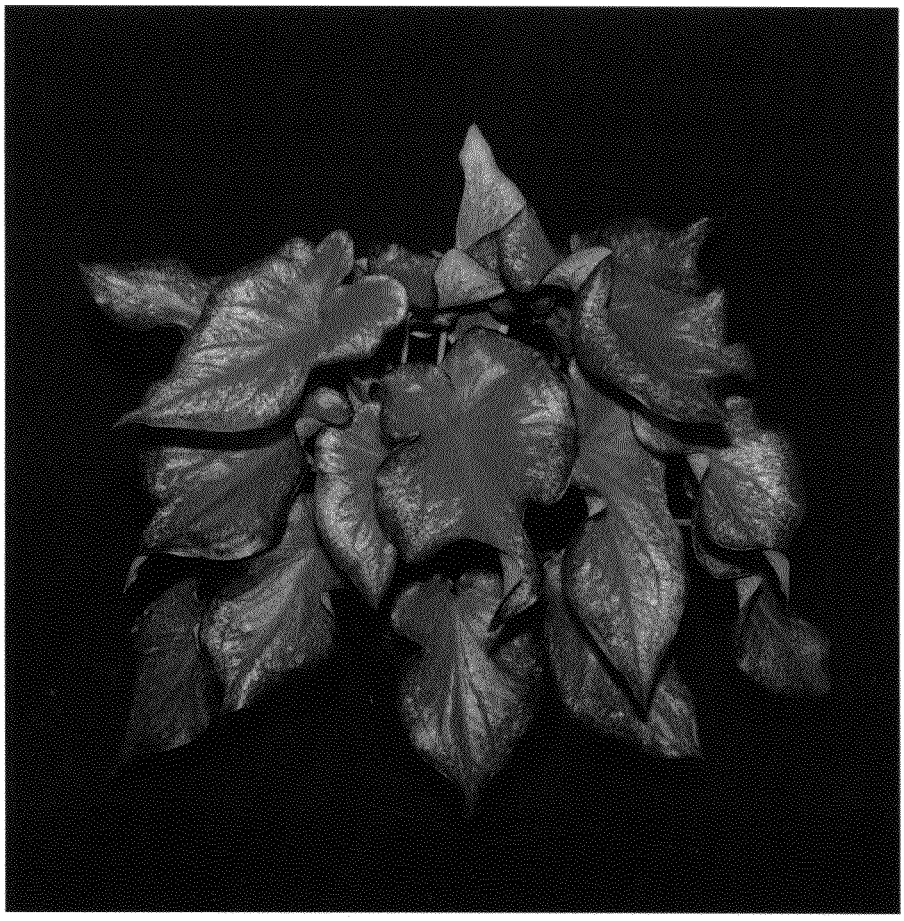

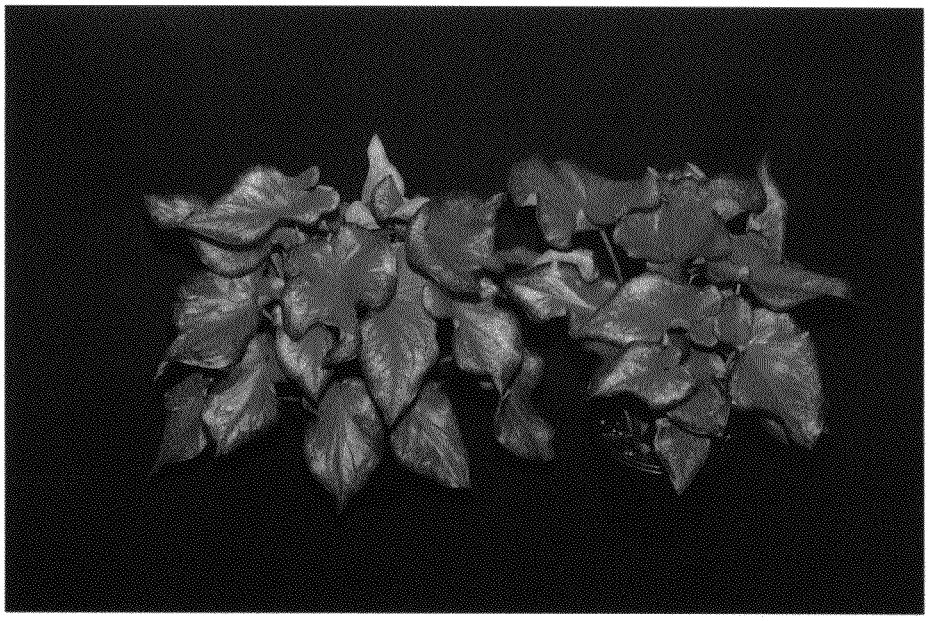
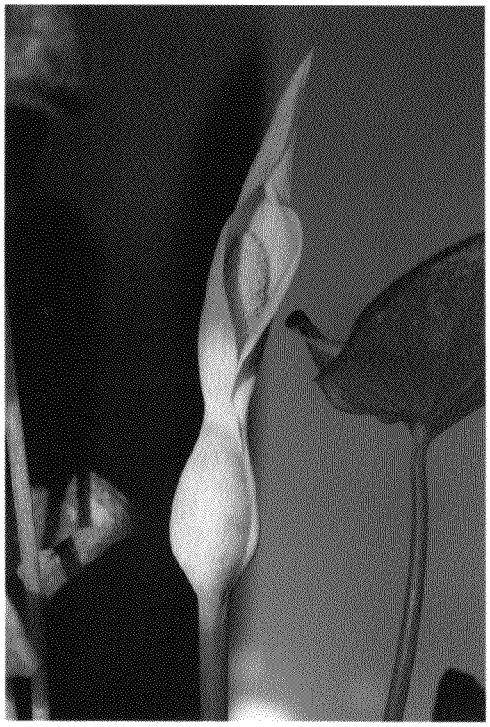

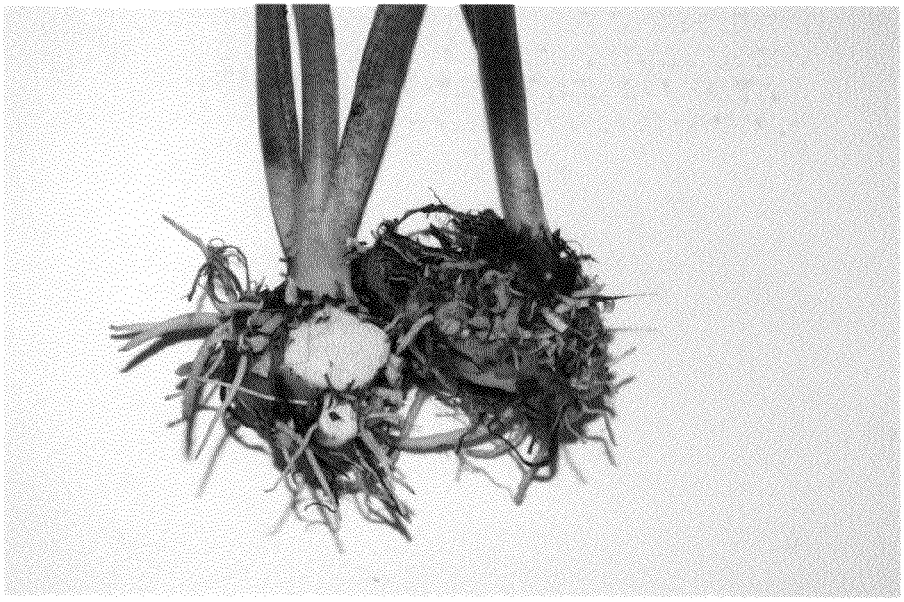
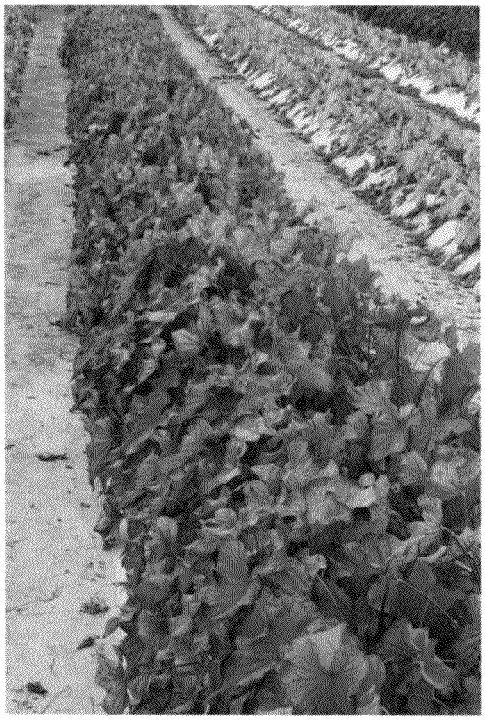

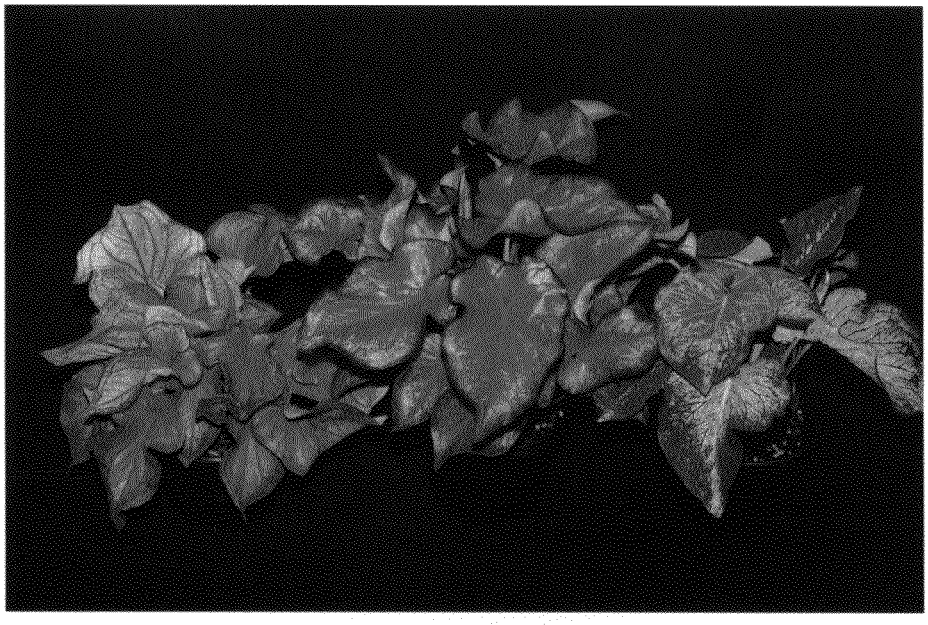
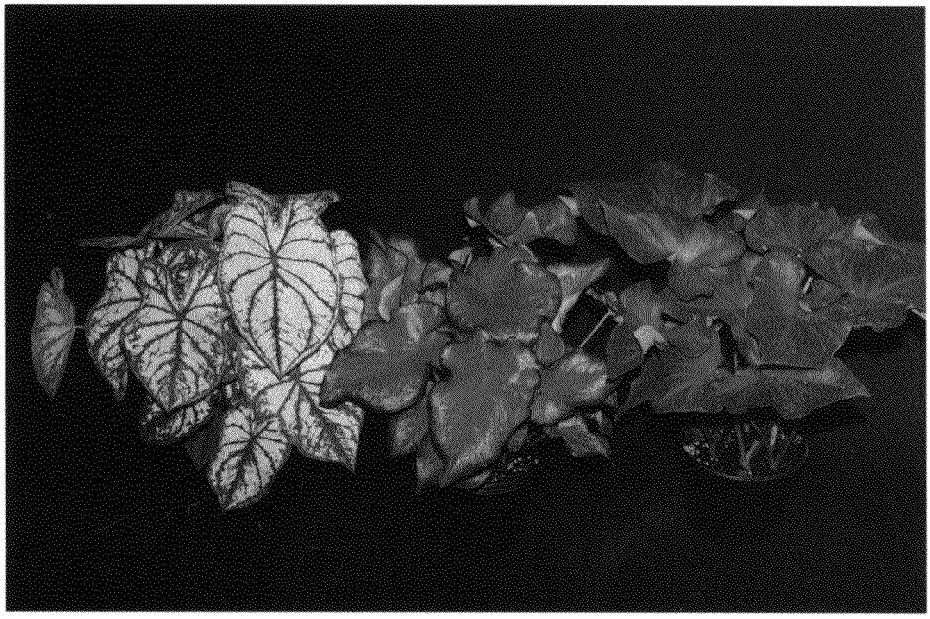

* * * * *